United States Patent
Kawakami et al.

(10) Patent No.: US 8,772,570 B2
(45) Date of Patent: Jul. 8, 2014

(54) LIQUID-ABSORBENT STRUCTURE FOR WEARING ARTICLE

(75) Inventors: Yasuke Kawakami, Kagawa (JP); Akane Sakai, Kagawa (JP); Ayako Akahira, Kagawa (JP)

(73) Assignee: Unicharm Corporation, Ehime (JP)

( * ) Notice: Subject to any disclaimer, the term of this patent is extended or adjusted under 35 U.S.C. 154(b) by 538 days.

(21) Appl. No.: 13/126,231

(22) PCT Filed: Oct. 19, 2009

(86) PCT No.: PCT/JP2009/068020
§ 371 (c)(1),
(2), (4) Date: Apr. 27, 2011

(87) PCT Pub. No.: WO2010/050376
PCT Pub. Date: May 6, 2010

(65) Prior Publication Data
US 2011/0208147 A1  Aug. 25, 2011

(30) Foreign Application Priority Data

Oct. 29, 2008  (JP) ................................. 2008-278780

(51) Int. Cl.
*A61F 13/15* (2006.01)
(52) U.S. Cl.
USPC ........... 604/378; 604/379; 604/380; 604/382; 604/385.101; 604/367; 604/368
(58) Field of Classification Search
USPC .......... 604/378, 379, 380, 382, 385.101, 367, 604/368
See application file for complete search history.

(56) References Cited

U.S. PATENT DOCUMENTS

| 3,879,257 | A | * | 4/1975 | Gentile et al. ................ 162/112 |
| 5,149,335 | A | * | 9/1992 | Kellenberger et al. ........ 604/372 |

(Continued)

FOREIGN PATENT DOCUMENTS

| JP | 60-63043 A | 4/1985 |
| JP | 2872851 B2 | 1/1999 |

(Continued)

OTHER PUBLICATIONS

International Search Report from corresponding PCT application No. PCT/JP2009/068020 dated Jan. 19, 2010.

*Primary Examiner* — Jacqueline F. Stephens
(74) *Attorney, Agent, or Firm* — Brinks Gilson & Lione

(57) ABSTRACT

A liquid-absorbent structure configured to prevent a liquid-absorbent core material from being unevenly distributed and thereby to assure that bodily fluids can be smoothly absorbed by the liquid-absorbent structure. According to one embodiment the present invention provides a panty liner that includes a topsheet lying on a side facing the wearer's body, a backsheet facing the wearer's garment and a liquid-absorbent structure sandwiched between these sheets. A first inner surface of a first sheet forming the liquid-absorbent structure is coated with adhesives to form a plurality of first bonding regions and a second inner surface of a second sheet is coated with adhesives to form a plurality of second bonding regions. Each of the first non-bonding regions lies between each pair of the first bonding regions, and each of the second non-bonding regions lies between each pair of the second bonding regions. The first inner surface and the second inner surface face each other, the first bonding regions face the second non-bonding regions via the liquid-absorbent core material, and the second bonding regions face the first non-bonding regions via the liquid-absorbent core material.

20 Claims, 10 Drawing Sheets

(56) References Cited

U.S. PATENT DOCUMENTS

| | | |
|---|---|---|
| 5,865,824 A | 2/1999 | Chen et al. |
| 2006/0278335 A1 | 12/2006 | Moriura et al. |
| 2007/0142802 A1 | 6/2007 | Suzuki |
| 2008/0038504 A1 | 2/2008 | Manabe et al. |

FOREIGN PATENT DOCUMENTS

| | | |
|---|---|---|
| JP | 2002-510993 A | 4/2002 |
| JP | 2005-059579 | 3/2005 |
| JP | 2005-253851 | 9/2005 |
| JP | 2006-006741 | 1/2006 |
| WO | WO 98/47455 A3 | 10/1998 |

* cited by examiner

LIQUID-ABSORBENT STRUCTURE FOR WEARING ARTICLE

RELATED APPLICATION

This application is a 35 U.S.C. §371 national phase filing of International Patent Application No. PCT/JP2009/068020, filed Oct. 19, 2009, through which and to which priority is claimed under 35 U.S.C. §119 to Japanese Patent Application No. 2008-278780, filed Oct. 29, 2008.

TECHNICAL FIELD

The present invention relates to liquid-absorbent structures and more particularly to liquid-absorbent structures having outstanding ability to absorb and to contain bodily fluids and being useful in various kinds of wearing articles, for example, panty liners for mucosal fluid, tissue or the like discharged from female genitals generically known as vaginal discharge, sanitary napkins or sanitary pads, or disposable diapers.

RELATED ART

Conventionally, absorbent articles adapted to be used in the wearer's crotch region are known, for example, from JP 60-63043 A (PATENT DOCUMENT 1) and JP 2872851 B2 (PATENT DOCUMENT 2). In the case of PATENT DOCUMENT 1, the water-absorbent resins are sandwiched between top- and backsheets to form the water-absorbent sheet. The inner side of the backsheet is coated with water-soluble resinous binders and thereby the water-absorbent resins are fixed between the top- and backsheets.

In the case of PATENT DOCUMENT 2, the absorbent structure comprises absorbent materials such as absorbent polymer particles (resins) and fluff wood pulp. An absorbent sheet is coated with adhesives in the form of dots, straight lines or curved lines, then absorbent polymer particles are sprayed thereon and the similar absorbent sheet is placed thereon. This assembly is then integrally compressed. The absorbent polymer particles are fixed to the absorbent sheets not only with the adhesives but also by being caught in fiber interstices of the absorbent sheets.

PRIOR ART DOCUMENT

Patent Document

PATENT DOCUMENT 1: JP 60-63043 A
PATENT DOCUMENT 2: JP 2872851 B2

DISCLOSURE OF THE INVENTION

Problem to be Solved by the Invention

According to the disclosure of PATENT DOCUMENT 1, the backsheet is coated over its entire area with binders so that the top- and backsheet are bonded to each other together with the water-absorbent resins sandwiched therebetween. The water-absorbent resins can be fixed by the top- and backsheets over the entire area thereof and thereby it is possible to prevent the water-absorbent resins from being unevenly distributed in a longitudinal direction as well as in a transverse direction. However, in a region of the topsheet bonded to the backsheet with binder with which the backsheet is coated, the liquid-perviousness is deteriorated. Liquid which has not been absorbed by the absorbent structure spreads over the topsheet and may leak out.

According to the disclosure of PATENT DOCUMENT 2, the absorbent polymer particles can be fixed to the absorbent sheets defining the upper and lower surfaces in the form of dots, straight lines or curved lines and therefore the desired liquid-perviousness should not be deteriorated. However, a certain quantity of the absorbent polymer particles not kept in contact with the adhesives may move in the longitudinal direction as well as in the transverse direction, so that the absorbent polymer particles may be unevenly distributed. Particularly when the absorbent sheets are not used but the absorbent polymer particles are directly sandwiched between top- and backsheet, freedom degree of the absorbent polymer particles increases and the possibility that the distribution of the polymer particles become localized will more increase.

It is an object of the present invention to provide a liquid-absorbent structure improved to prevent the liquid-absorbent core materials from being unevenly distributed and thereby to assure that bodily fluids can be smoothly absorbed by the liquid-absorbent structure.

Measure to Solve the Problem

According to the present invention, there is provided a liquid-absorbent structure for a wearing article having a longitudinal direction and a transverse direction and comprising a first sheet, a second sheet opposed to the first sheet and a liquid-absorbent core material sandwiched between the first and second sheets.

The present invention is characterized in that: at least one of the first and second sheets is liquid-pervious; the first sheet has a first inner surface facing the liquid-absorbent core material and a first outer surface opposed to the first inner surface and the second sheet has a second inner surface facing the liquid-absorbent core material and a second outer surface opposed to the second inner surface; the first inner surface and the second inner surface respectively comprise first and second bonding regions respectively formed with bonding means used to bond the liquid-absorbent core material to the first and second inner surfaces, and further comprise first and second non-bonding regions having no bonding means; and the first bonding regions face at least the second non-bonding regions and the second bonding regions face at least the first non-bonding regions.

According to an embodiment of the present invention, a plurality of the first and second bonding regions extend in the longitudinal direction and are spaced one from another in the transverse direction so that each of the first non-bonding regions lies between each pair of the first bonding regions and each of the second non-bonding regions lies between each pair of the second bonding regions.

According to another embodiment of the present invention, the first non-bonding regions respectively have a length dimension in the transverse direction larger than that of the respective second bonding regions facing the first non-bonding regions and the second non-bonding regions respectively have a length in the transverse direction larger than that of the respective first bonding regions facing the first bonding regions.

According to still another embodiment of the present invention, the first sheet lies on a side facing the wearer's body and the second sheet lies on a side opposed to the side facing the wearer's body; and the first and second sheets respectively have first side edges and second side edges extending in the longitudinal direction in such a manner that the second side edges extend outward beyond the first side edges in the transverse direction and portions of the second sheet extending beyond the first side edges are folded back along the first side edges onto the first outer surface and bonded to the first outer surface.

According to yet another embodiment of the present invention, the liquid-absorbent core material comprises at least absorbent polymer particles.

According to further another embodiment of the present invention, the second sheet is additionally formed on the second outer surface with a high density liquid-absorbent structure; the first and second sheets are liquid-pervious;

the high density liquid-absorbent structure comprises liquid-absorbent core material and a wrapping sheet used to wrap the liquid-absorbent core material, the high density liquid-absorbent structure is at least partially formed with high density regions having a higher density of the liquid-absorbent core material than that in the remaining region.

According to an alternative embodiment of the present invention, the high density regions in the high density liquid-absorbent structure overlap at least anyone of the first and second non-bonding regions.

Effect of the Invention

In the liquid-absorbent structure according to the present invention, at least one of the first sheet and the second sheet sandwiching the liquid-absorbent core material is liquid-pervious, the first inner surface of the first sheet and the second inner surface of the second sheet respectively comprise the first and second bonding regions which are formed with the bonding means used to bond the liquid-absorbent core material and further comprise the first and second non-bonding regions which are not formed with any bonding means, wherein the first bonding regions face at least the second non-bonding regions and the second bonding regions face at least the first non-bonding regions. With such arrangement, it is ensured that the first and second sheets are formed with the first or second non-bonding regions which are permeable to bodily fluids, and through the regions, bodily fluids can be absorbed by the liquid-absorbent core material. Once bodily fluids have been absorbed by the liquid-absorbent core material, bodily fluids should not leak out by moving on the surface of first or second sheet. Furthermore, the liquid-absorbent core material is reliably contained in the first or second bonding regions and thereby it is possible to prevent the liquid-absorbent core material from being unevenly distributed.

BRIEF DESCRIPTION OF THE DRAWINGS

FIG. 1 is a plan view of a panty liner according to a first embodiment.

FIG. 2 is a sectional view taken along line II-II in FIG. 1.

FIG. 3 is a schematic diagram illustrating a liquid-absorbent structure.

FIG. 4(a) is a schematic diagram illustrating a first sheet as viewed from the side of a first inner surface and FIG. 4(b) is a schematic diagram illustrating a second sheet as viewed from the side of a second inner surface.

FIG. 5 is a plan view of a panty liner according to a second embodiment.

FIG. 6 is a sectional view taken along line VI-VI in FIG. 5.

FIG. 7 is a plan view of a liquid-absorbent structure.

FIG. 8(a) is a schematic diagram illustrating the first sheet according to a third embodiment as viewed from the side of the first inner surface and FIG. 8(b) is a schematic diagram illustrating the second sheet according to the third embodiment as viewed from the side of the second inner surface.

FIG. 9 is a plan view of a panty liner according to a fourth embodiment.

FIG. 10 is a sectional view taken along line X-X in FIG. 9.

DETAILED DESCRIPTION OF THE PREFERRED EMBODIMENTS

Details of the liquid-absorbent structure according to the present invention adapted to be used in the form of a wearing article will be exemplarily described hereunder.

<First Embodiment>

Figure 1:
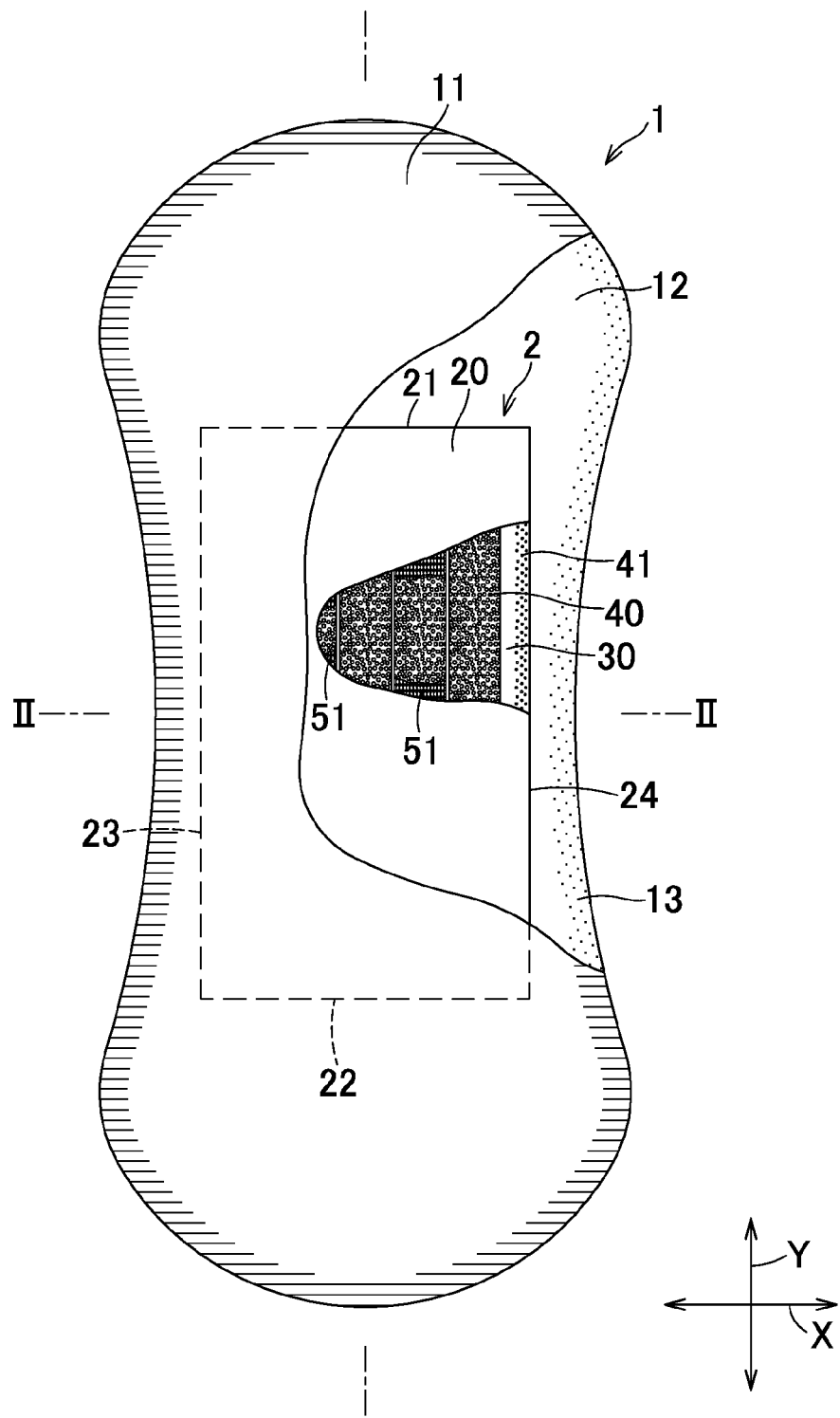
[FIG. 1]
Figure 2:
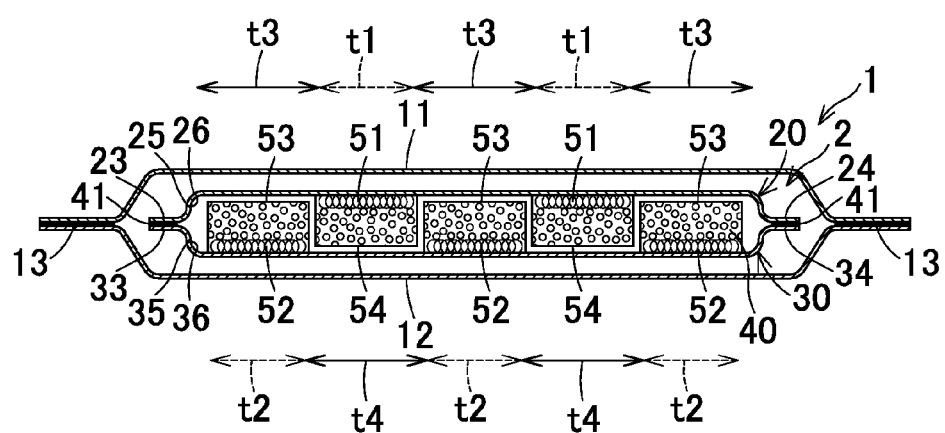
[FIG. 2]

This is the case in which the liquid-absorbent structure is implemented in the form of a panty liner 1 primarily to absorb and contain urine. FIG. 1 is a partially cutaway plan view of the panty liner 1 and FIG. 2 is a sectional view taken along line II-II in FIG. 1. The panty liner 1 has a longitudinal direction Y and a transverse direction X orthogonal thereto and is shaped to be relatively long in the longitudinal direction Y. The panty liner 1 comprises a topsheet 11 lying on a side facing the wearer's body, a backsheet 12 facing the wearer's garment such as a sanitary panty and a liquid-absorbent structure 2 sandwiched between these sheets 11, 12. The top- and backsheets 11, 12 are bonded to each other along respective peripheral edges thereof by a bonding region 13.

Figure 3:
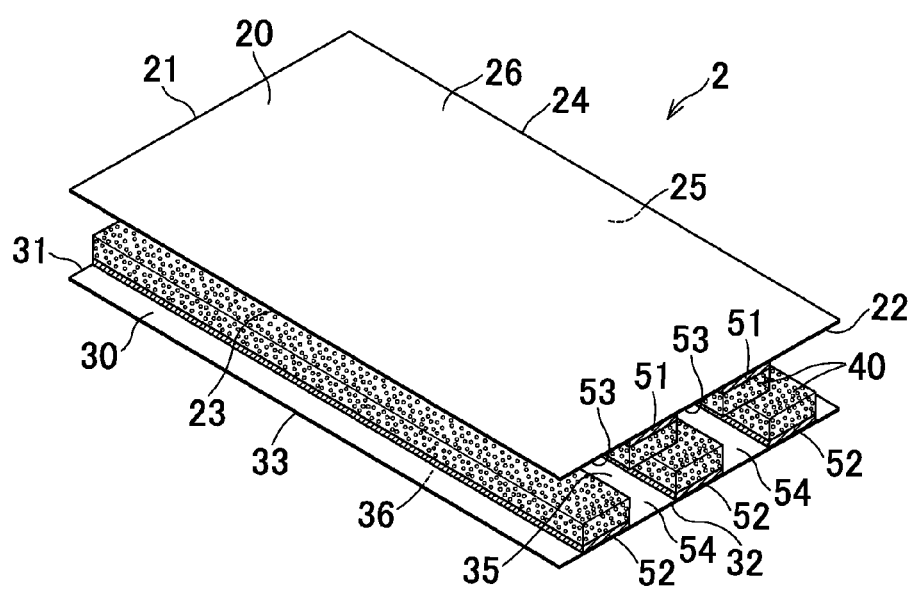
[FIG. 3]

The liquid-absorbent structure 2 comprises a first sheet 20 lying on the side facing the wearer's body and bonded to the topsheet 11, a second sheet 30 lying on the side facing the wearer's garment and bonded to the backsheet 12, and a liquid-absorbent core material 40 sandwiched between the first and second sheets 20, 30. FIG. 3 is a schematic diagram illustrating the liquid-absorbent structure 2, FIG. 4(a) is illustrating the first sheet 20 as viewed from the side of a first inner surface 25 and FIG. 4(b) is illustrating a second sheet 30 as viewed from the side of a second inner surface 25 in (b). The first sheet 20 is contoured by opposite ends 21, 22 extending in the transverse direction X and opposite side edges 23, 24 extending in the longitudinal direction Y and the second sheet 30 also is contoured by opposite ends 31, 32 extending in the transverse direction X and opposite side edges 33, 34 extending in the longitudinal direction Y. The first sheet 20 and the second sheet 30 are bonded together along the ends 21, 22 as well as the opposite side edges 23, 24 of the first sheet 20 in such a way that the ends 31, 32 and the opposite side edges 33, 34 of the second sheet 30 are completely overlapped with each other.

The first sheet 20 has a first inner surface 25 facing the liquid-absorbent core material 40 and a first outer surface 26 facing the topsheet 11 and the second sheet 30 has a second inner surface 35 facing the liquid-absorbent core material 40 and a second outer surface 36 facing the backsheet 12.

The liquid-absorbent core material 40 is formed of superabsorbent polymer particles or wood pulp fibers which are both well known, and bonded to the first inner surface 25 and the second inner surface 35 by suitable bonding means. The first inner surface 25 may be coated with the bonding adhesives such as hot melt adhesives to define a first bonding region 51 and the second inner surface 35 may be coated with such adhesives to define a second bonding region 52.

A plurality of the first bonding regions 51 and a plurality of the second bonding regions 52 are formed and they extend in the longitudinal direction Y and are spaced one from another in the transverse direction X so that a first non-bonding region 53 is defined between each pair of the adjacent first bonding regions 51 and a second non-bonding region 54 is defined between each pair of the adjacent second bonding regions 52. The first inner surface 25 of the first sheet 20 and the second inner surface 35 of the second sheet 30 face each other, sandwiching the liquid-absorbent core material 40 therebetween. In this state, the first bonding regions 51 face the second non-bonding regions 54 with the liquid-absorbent core material 40 interposed therebetween and the second bonding regions 52 face the first non-bonding region 53 with the liquid-absorbent core material 40 interposed therebetween.

Referring to FIG. 2, the respective first bonding regions 51 have a length dimension t1 in the transverse direction X smaller than a length dimension t4 of to have a length dimension t1 in the transverse direction X of the respective second non-bonding region 54. The respective second bonding regions 52 have a length dimension t2 in the transverse direction X smaller than a length dimension t3 in the transverse direction X of the respective first non-bonding region 53. According to this embodiment, the dimension t1 is substantially equal to the dimension t2 and the dimension t3 is substantially equal to the dimension t4.

These first and second bonding regions 51, 52 are obtained by coating the first inner surface 25 and the second inner surface 35 with hot melt adhesives using a coater. By using the coater to coat these inner surfaces 25, 35 with hot melt adhesives, the first and second bonding regions 51, 52 can be dimensioned in the transverse direction X with a sufficiently high degree of accuracy to prevent the first and second bonding regions 51, 52 from overlapping in the thickness direction.

The liquid-absorbent core material 40 is distributed on the inner surface of one of the first and second sheets 20, 30 formed with the first and second bonding regions 51, 52 and then the other sheet 20 or 30 is placed thereon so that the first bonding regions 51 may face the second non-bonding regions 54 and the second bonding regions 52 may face the first non-bonding regions 53. Thereby the liquid-absorbent core material 40 is fixed in the first and second bonding regions 51, 52.

The first and second sheets 20, 30 are formed along respective peripheral edges thereof with a bonding region 41 along which the first and second sheets 20, 30 are directly bonded to each other to prevent the liquid-absorbent core material 40 from falling off.

In the panty liner 1 having such liquid-absorbent structure 2, the first bonding regions 51 and the second bonding regions are alternately formed in the transverse direction X. Consequentially, the liquid-absorbent core material 40 is bonded to the first bonding regions 51 of the first sheet 20 or the second bonding regions 52 of the second sheet 30. In this way, move of the liquid-absorbent core material 40 can be prevented from moving between the first and second sheets 20, 30, so that uneven distribution of the liquid-absorbent core material 40 can be restricted. In this way, it is possible to contain the liquid-absorbent core material 40 evenly in the longitudinal direction Y as well as in the transverse direction X.

The first sheet 20 is formed with the first bonding regions 51 and the first non-bonding region 53 alternately in the transverse direction X and, with such arrangement, bodily fluids discharged onto the panty liner 1 should not be partially left on the first sheet 20 without being absorbed by the liquid-absorbent core material 40. Assumed that the first sheet 20 is coated over the entire area of the first inner surface 25 with adhesives, the adhesives will interfere with flowing of bodily fluids into the liquid-absorbent core material 40 and a certain quantity of bodily fluids will be left on the first sheet 20. The quantity of bodily fluids left on the sheet will move on the sheet and leak out of the panty liner 1. According to the present embodiment, however, bodily fluids can flow through the first non-bonding regions 53 into the liquid-absorbent core material 40 and thus leakage of bodily fluids may be restricted.

It should be noted that the first and second bonding regions 51, 52 are not limited to those which are perfectly liquid-impervious and it is also possible to use those having a certain degree of liquid-perviousness.

Alternate arrangement of the first and second bonding regions 51, 52 in the transverse direction X assures that the first and second sheets 20, 30 are not bonded to each other except along the respective peripheral edges of these two sheets 20, 30. In consequence, the first and second sheets 20, 30 can be spaced from each other. While the liquid-absorbent core material 40 will be swollen and become bulky upon absorption of bodily fluids, the liquid-absorbent core material 40 should not be hindered its swollenness and absorption capacity since the first and second sheets 20, 30 can be spaced from each other in response to absorption of bodily fluids by the liquid-absorbent core material 40.

The first and second non-bonding regions 53, 54 respectively have the dimensions t3, t4 larger than the dimensions t1, t2 of the first and second bonding regions 51, 52, respectively, and therefore it is possible to prevent the first and second bonding regions 51, 52 from overlapping each other in the thickness direction. If these bonding regions overlap each other in the thickness direction, separation of the first and second sheets 20, 30 from each other will be hampered. By arranging the first and second bonding regions in such a dimensional relation as described above, the present embodiment assures that bodily fluids are guided to the first non-bonding regions 53, and then, through the first bonding region 51 and the second bonding region 52, to the second non-bonding region 54. By creating such flow of bodily fluids, bodily fluids may quickly move to the side of the second sheet 30, i.e., move away from the side facing the wearer's body, so that it is possible to prevent bodily fluids from being partially left on the side of the first sheet 20 facing the wearer's body for a prolonged time. If bodily fluids are partially left on the side of the first sheet 20 facing the wearer's body, bodily fluids may flow on the first sheet 20, causing leakage of bodily fluids and/or cling on the wearer's skin, causing skin trouble such as eczema.

The dimensions t1 and t2 of the first and second bonding regions 51, 52 are preferably in a range of 1 mm to 80 mm. The dimensions t1 and t2 smaller than 1 mm will make it difficult to fix the absorbent polymer particles of the liquid-absorbent core material 40 in a reliable manner and there is a possibility that the absorbent polymer particles might fall off from the first and second sheets 20, 30. This is for the reason that, when the absorbent polymer particles are used in the form of particles, the average particle diameter is in a range of 300 μm to 400μm. The dimensions t1 and t2 of 80 mm or larger will make bodily fluids difficult to move rapidly to the liquid-absorbent core material 40.

While the first and second bonding regions 51, 52 are arranged alternately in the transverse direction X between the first and second sheets 20, 30 overlapped with each other according to the present embodiment, it is not essential that the first and second bonding regions 51, 52 alternate. For example, an alternative arrangement is possible such that the two or more second bonding regions 52 arranged between a pair of the first bonding regions 51. As another alternative arrangement, the first and second bonding regions 51, 52 may be arranged alternately in the longitudinal direction Y and in the transverse direction X in a checkered pattern. The first and second bonding regions 51, 52 can be arranged in any form so far as the first and second bonding regions 51, 52 are not overlapping each other in the thickness direction.

By preventing the first and second bonding regions 51, 52 from overlapping each other, a desired flexibility of the first and second sheets 20, 30 may be maintained in comparison to the case in which the first and second bonding regions 51, 52 more or less overlap each other in the thickness direction.

The first and second sheets 20, 30 maybe formed, for example, of liquid-pervious fibrous nonwoven fabrics. According to the present embodiment, at least the first sheet 20 is required to be liquid-pervious and, so far as this requirement is met, various types of well known sheet materials may be used to form these first and second sheets 20, 30.

While the superabsorbent polymer particles are used as the liquid-absorbent core material 40 according to the present embodiment, it is possible to use the other types of core materials such as wood pulp and it is also possible to combine these different types of material to obtain the liquid-absorbent core material 40.

<Second Embodiment>

Figure 5:
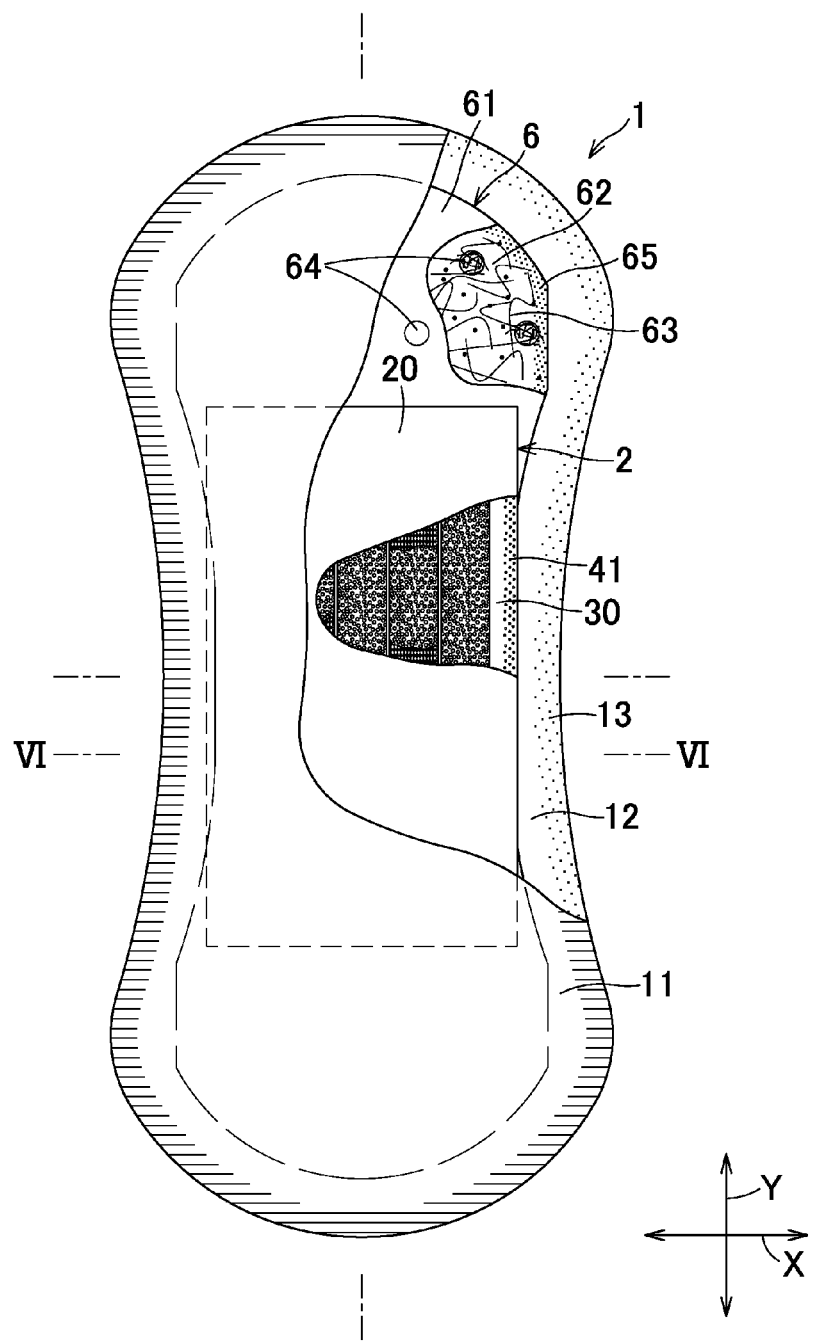
[FIG.5]
Figure 6:
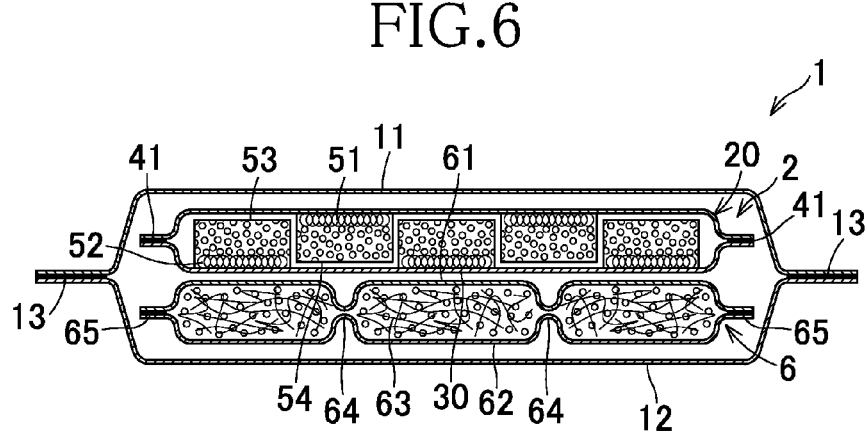
[FIG. 6]

FIG. 5 is a plan view of a panty liner according to a second embodiment and FIG. 6 is a sectional view taken along line VI-VI in FIG. 5. The second embodiment is characterized in that the panty liner 1 further comprises a high density liquid-absorbent structure 6. The other component elements are similar to those in the first embodiment and description thereof will not be repeated hereunder.

The high density liquid-absorbent structure 6 is placed on the side of the liquid-absorbent structure 2 facing the wearer's garment, more specifically, placed on the side of the second sheet 30 of the liquid-absorbent structure 2 facing the wearer's garment, i.e., to the side of the second outer surface 36. The panty liner 1 comprises the topsheet 11, the liquid-absorbent structure 2, the high density liquid-absorbent structure 6 and backsheet 12 placed in this order from the side facing the wearer's body to the side facing the wearer's garment. The high density liquid-absorbent structure 6 comprises a first wrapping sheet 61 lying on the side facing the wearer's body, a second wrapping sheet 62 lying on the side facing the wearer's garment and a liquid-absorbent core material 63 sandwiched between these sheets 61, 62. The first and second wrapping sheets 61, 62 cooperate with each other to define the wrapping sheet according to the present embodiment and are bonded together along opposite side edges with bonding regions 65. The liquid-absorbent core material 63 may be formed of a mixture of fluff wood pulp and superabsorbent polymer particles or one of them. As the first and second wrapping sheets 61, 62, dispersant tissue papers may be used. The high density liquid-absorbent structure 6 has an area larger than that of the liquid-absorbent structure 2 and a shape which is generally similar to the shape of the top- and backsheets 11, 12 so as to be contoured along the inner peripheral edges of these sheets 11, 12.

Figure 7:
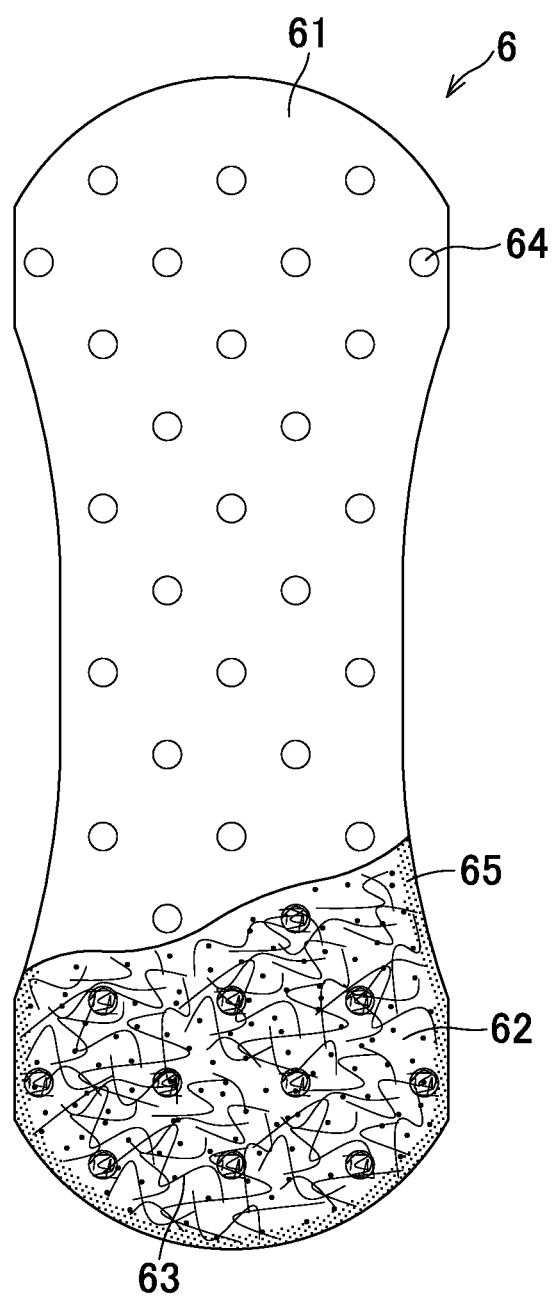
[FIG. 7]

FIG. 7 is a plan view showing a high density liquid-absorbent structure 6 as partially cutaway for convenience of explanation. As shown in FIG. 7, the high density liquid-absorbent structure 6 is formed with high density regions 64 distributed over its entire area. The high density regions 64 are formed of locally compressing the first and second wrapping sheets 61, 62 together with the liquid-absorbent core material 63 in the form of dots intermittently distributed in the longitudinal direction Y as well as in the transverse direction X. The high density regions 64 are concavely depressed from the first wrapping sheet 61 through the liquid-absorbent core material 63 to the side of the second wrapping sheet 62. The liquid-absorbent core material 63 is compressed in the high density regions 64 in which the liquid-absorbent core material 63 has a density higher in the remaining region.

Referring to FIG. 6, the high density regions 64 of the high density liquid-absorbent structure 6 are formed so as to overlap the second non-bonding regions 54 of the liquid-absorbent structure 2 lying on the side of the high density regions 64 facing the wearer's body.

With such arrangement of the high density regions 64, it is assured that bodily fluids having flown into the liquid-absorbent structure 2 are guided through the first non-bonding regions 53, then through the second non-bonding regions 54 and finally into the high density regions 64 of the high density liquid-absorbent structure 6. In other words, it is possible to guide bodily fluids from the liquid-absorbent structure 2 defining the upper layer to the high density liquid-absorbent structure 6 defining the lower layer through the high density regions 64 and thereby to accelerate the movement of bodily fluids away from the wearer's body.

While high density regions 64 are obtained by compression work in the pattern of dots intermittently distributed according to the present embodiment, the pattern of these regions 64 is not limited to the pattern of dots but maybe appropriately selected from the other patterns such as line segment pattern. It is also possible to compress only the high density liquid-absorbent structure 6 or to compress the liquid-absorbent structure 2 defining an upper layer and the high density liquid-absorbent structure 6 defining a lower layer at once after these upper and lower layers have been overlapped with each other.

Furthermore, it is also possible to use the other kinds of treatments other than compression to form the high density regions 64.

<Third Embodiment>

Figure 4:
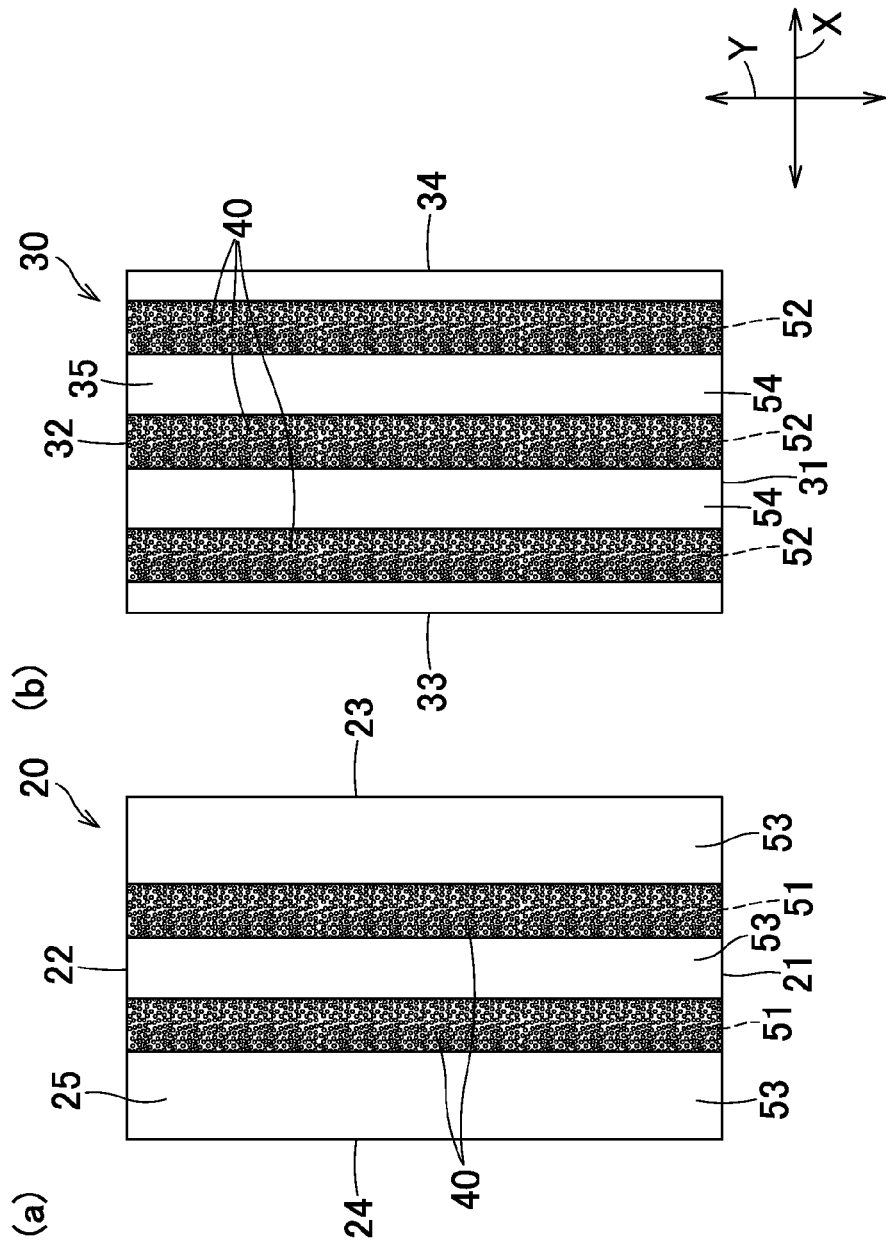
[FIG. 4]
Figure 8:
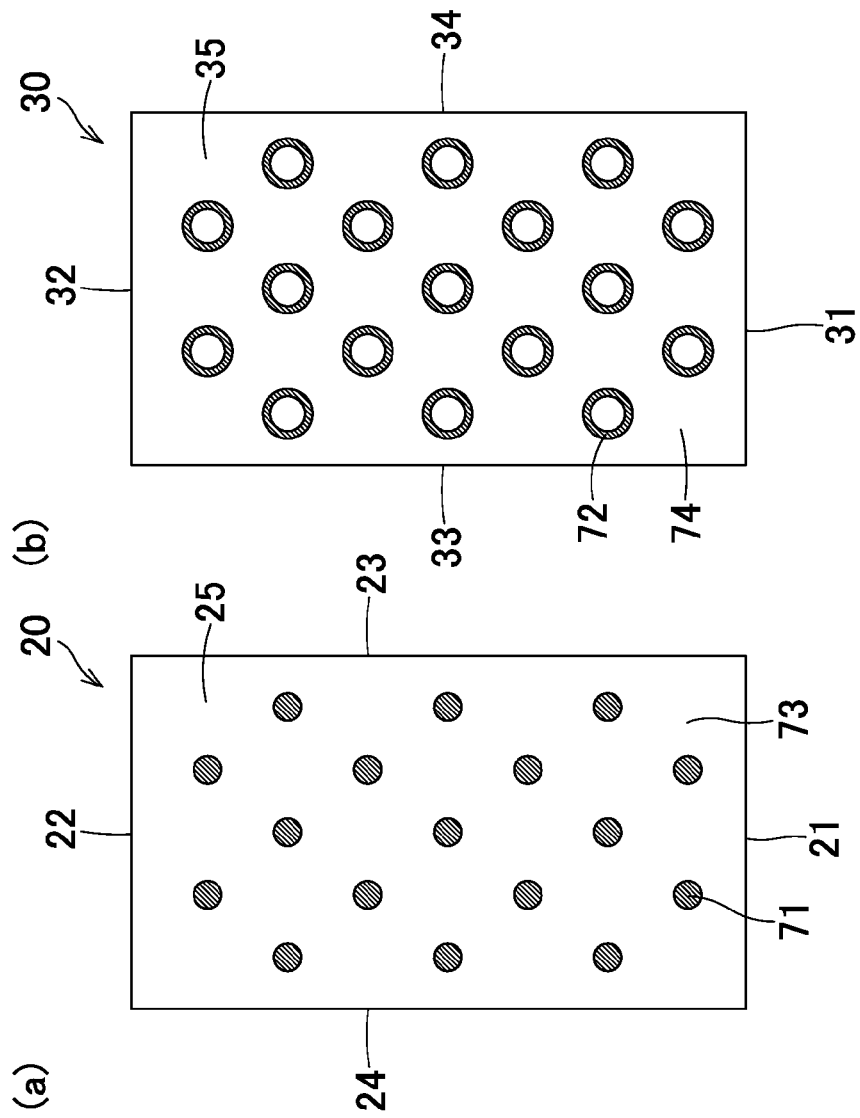
[FIG. 8]

FIG. 8 is a schematic diagram similar to FIG. 4 of the first embodiment, illustrating a third embodiment. The third embodiment is similar to the first embodiment except the configuration of the first and second bonding regions as well as the configuration of the first and second non-bonding regions. The other component elements are similar to those and description thereof will not be repeated hereunder.

FIG. 8(a) is a schematic diagram illustrating the first sheet 20 as viewed from the side of the first inner surface 25 and FIG. 8(b) is a schematic diagram illustrating the second sheet 30 as viewed from the side of the second inner surface 35. As illustrated in FIG. 8, the first sheet 20 is formed on the first inner surface 25 thereof with first bonding regions 71 coated with adhesives and a first non-bonding region 73 not coated with adhesives. The first bonding regions 71 are formed over the entire area of the first inner surface 25 of the first sheet 20 in the form of dots intermittently distributed in the longitudinal direction Y as well as in the transverse direction X. The region other than these first bonding regions 71 defines the first non-bonding region 73.

The second sheet 30 is formed on the second inner surface 35 thereof with second bonding regions 72 coated with adhesives and second non-bonding regions 74. The second bonding regions 72 are formed over the entire area of the second inner surface 35 generally in the form of circles intermittently distributed and each of the circles defines in the vicinity of its center non-bonding regions. In other words, each of the second bonding regions 72 is so-called doughnut-shaped and the second non-bonding regions 74 are defined in the vicinity of the centers and outer circumferences of the second bonding regions 72.

The respective first bonding regions 71 are arranged to face the second non-bonding regions 74 defined in the vicinity of the respective centers of the second bonding regions 72 and dimensioned to have areas smaller than those of the second non-bonding regions 74 defined in the vicinity of the respective centers. The second bonding regions 72 at least partially face the first non-bonding region 73. Consequentially, the first inner surface 25 of the first sheet 20 can be placed on the second inner surface 35 of the second sheet 30 so that the first bonding regions 71 may not overlap the second bonding regions 72 in the thickness direction thereof. The first bonding regions 71 and the second bonding regions 72 can be spaced one from another in the longitudinal direction Y as well as in the transverse direction X and thereby bodily fluids can be facilitated to flow into the liquid-absorbent core material in the longitudinal direction Y as well as in the transverse direction X. In this way, the possibility of leakage of bodily fluids from the side of the first sheet 20 facing the wearer's body may be further reduced.

<Fourth Embodiment>

Figure 9:
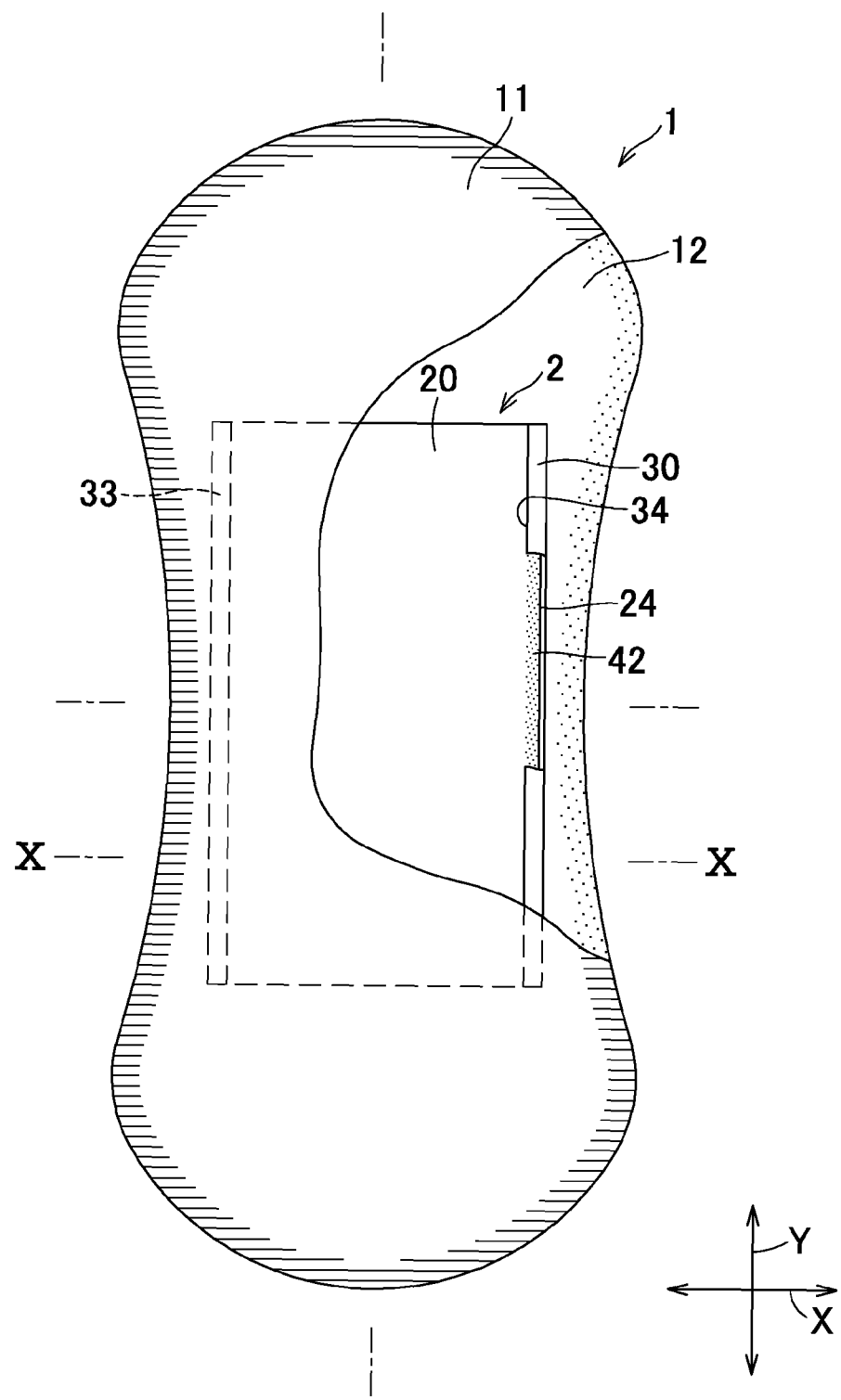
[FIG. 9]
Figure 10:
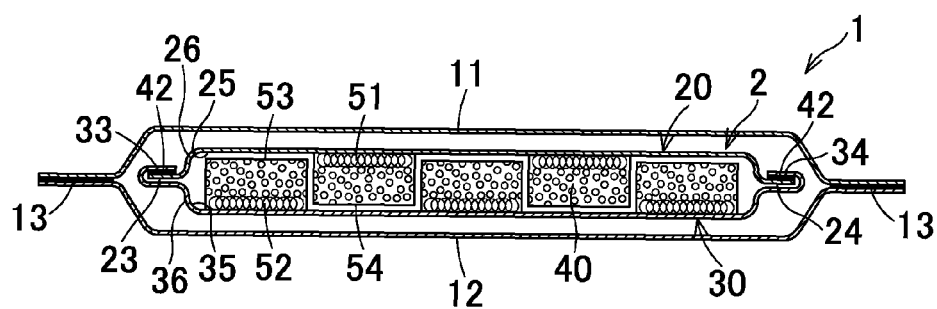
[FIG. 10]

FIGS. 9 and 10 are diagrams illustrating the panty liner 1 according to a fourth embodiment wherein FIG. 9 is a plan view of the panty liner 1 and FIG. 10 is a sectional view taken along line X-X in FIG. 9. The fourth embodiment is similar to the first embodiment except bonding regions 42 along which the first and second sheets 20, 30 are bonded to each other. The other component elements are similar to those in the first embodiment and the description thereof will not be repeated hereunder.

As shown in FIGS. 9 and 10, the second sheet 30 has an area larger than that of the first sheet 20 and the side edges 33, 34 of the second sheet 30 extend outward beyond the side edges 23, 24 of the first sheet 20. The side edges 33, 34 of the second sheet 30 extending outward beyond the side edges 23, 24 in this manner are folded back onto the side of the first sheet 20 facing the wearer's body and the second inner surface 35 of the edges folded back in this manner are bonded to the first outer surface 26 of the first sheet 20 to define the bonding regions 42.

By folding back and bonding the second sheet 30 facing the wearer's garment to the first outer surface 26 of the first sheet 20 lying on the side facing the wearer's body in the aforementioned manner, it is possible to prevent the liquid-absorbent core material 40 sandwiched between these first and second sheets 20, 30 from falling off. Specifically, by folding back the second sheet 30 lying on the side facing the wearer's garment toward the side facing the wearer's garment, the liquid-absorbent core material 40 can be contained by the second sheet 30 even if the first and second sheets 20, 30 are partially peeled off from each other. In this way, the liquid-absorbent core material 40 should not readily fall off.

In the first to fourth embodiments as described above, the techniques widely used in the relevant field such as adhesives, thermal or ultrasonic bonding may be selectively used to join the first and second sheets 20, 30 to each other. The topsheet may be formed, for example, of liquid-pervious and air-permeable fibrous nonwoven fabric and the backsheet 12 may be formed, for example, of liquid-impervious plastic films. Fibrous nonwoven fabrics may be additionally provided on the side of the backsheet 12 with a layer of fibrous nonwoven fabric in consideration of the texture of the panty liner 1.

While the first and second bonding regions are formed by coating the sheets with hot melt adhesives by using the coater in the aforementioned embodiments, the present invention is not limited to this but the conventional methods widely used in the relevant field may be selectively used so far as the liquid-absorbent core material can be bonded over a predetermined range to the sheets.

While the first sheet faces the wearer's body and the second sheet faces the wearer's garment in the aforementioned embodiments, it is possible to reverse the positional relation between these first and second sheets.

Identification of Reference Numerals Used in The Drawings
1 panty liner
2 liquid-absorbent structure
20 first sheet
25 first inner surface
26 first outer surface
30 second sheet
35 second inner surface
36 second outer surface
40 liquid-absorbent core
51 first bonding regions
52 second bonding regions
53 first non-bonding regions
54 second non-bonding regions
60 high density liquid-absorbent structure
61 first wrapping sheet
62 second wrapping sheet
63 liquid-absorbent core
64 high density regions
71 first bonding regions
72 second bonding regions
73 first non-bonding region
74 second non-bonding regions

The invention claimed is:

1. A liquid-absorbent structure for a wearing article having a longitudinal direction and a transverse direction, the liquid-absorbent structure comprising;
a first sheet;
a second sheet opposed to said first sheet; and
a liquid-absorbent core material sandwiched between said first and second sheets, wherein
at least one of said first and second sheets is liquid-pervious;
said first sheet has a first inner surface facing said liquid-absorbent core material and a first outer surface opposed to said first inner surface and said second sheet has a second inner surface facing said liquid-absorbent core material and a second outer surface opposed to said second inner surface;
said first inner surface and said second inner surface respectively comprise first and second bonding regions respectively formed with bonding means used to bond said liquid-absorbent core material to said first and second inner surfaces, and further comprise first and second non-bonding regions having no bonding means;
said first bonding regions face said second non-bonding regions exclusively, and said second bonding regions face said first non-bonding regions exclusively;
the first sheet is contoured by opposite ends extending in the transverse direction and opposite side edges extending in the longitudinal direction and the second sheet also is contoured by opposite ends extending in the transverse direction and opposite side edges extending in the longitudinal direction; and
the first sheet and the second sheet are bonded together exclusively along the ends as well as the opposite side edges of the first sheet and the second sheet being completely overlapped with each other.

2. The liquid-absorbent structure defined by claim 1, wherein a plurality of said first and second bonding regions extend in said longitudinal direction and are spaced one from another in said transverse direction so that each of said first non-bonding regions lies between each pair of said first bonding regions, and each of said second non-bonding regions lies between each pair of said second bonding regions.

3. The liquid-absorbent structure defined by claim 2, wherein said first non-bonding regions respectively have a length dimension in said transverse direction larger than that of respective said second bonding regions facing said first non-bonding regions, and said second non-bonding regions respectively have a length in said transverse direction larger than that of said first bonding regions facing said first bonding regions.

4. The liquid-absorbent structure defined by claim 3, wherein
said first sheet lies on a side facing the wearer's body and said second sheet lies on a side opposed to said side facing said wearer's body; and
said first and second sheets respectively have first side edges and second side edges extending in said longitudinal direction in such a manner that said second side edges extend outward beyond said first side edges in said transverse direction and portions of said second sheet extending beyond said first side edges are folded back along said first side edges onto said first outer surface and bonded to said first outer surface.

5. The liquid-absorbent structure defined by claim 4, wherein said liquid-absorbent core material comprises at least absorbent polymer particles.

6. The liquid-absorbent structure defined by claim 3, wherein said liquid-absorbent core material comprises at least absorbent polymer particles.

7. The liquid-absorbent structure defined by claim 2, wherein
said first sheet lies on a side facing the wearer's body and said second sheet lies on a side opposed to said side facing said wearer's body; and
said first and second sheets respectively have first side edges and second side edges extending in said longitudinal direction in such a manner that said second side edges extend outward beyond said first side edges in said transverse direction and portions of said second sheet extending beyond said first side edges are folded back along said first side edges onto said first outer surface and bonded to said first outer surface.

8. The liquid-absorbent structure defined by claim 7, wherein said liquid-absorbent core material comprises at least absorbent polymer particles.

9. The liquid-absorbent structure defined by claim 2, wherein said liquid-absorbent core material comprises at least absorbent polymer particles.

10. The liquid-absorbent structure defined by claim 2, wherein
said second sheet is additionally formed on said second outer surface with a high density liquid-absorbent structure;
said first and second sheets are liquid-pervious;
said high density liquid-absorbent structure comprises liquid-absorbent core material and a wrapping sheet used to wrap said liquid-absorbent core material, said high density liquid-absorbent structure being at least partially formed with high density regions having a density higher than that in the remaining region of said liquid-absorbent core material.

11. The liquid-absorbent structure defined by claim 1, wherein said first non-bonding regions respectively have a length dimension in said transverse direction larger than that of respective said second bonding regions facing said first non-bonding regions, and said second non-bonding regions respectively have a length in said transverse direction larger than that of said first bonding regions facing said first bonding regions.

12. The liquid-absorbent structure defined by claim 11, wherein
said first sheet lies on a side facing the wearer's body and said second sheet lies on a side opposed to said side facing said wearer's body; and
said first and second sheets respectively have first side edges and second side edges extending in said longitudinal direction in such a manner that said second side edges extend outward beyond said first side edges in said transverse direction and portions of said second sheet extending beyond said first side edges are folded back along said first side edges onto said first outer surface and bonded to said first outer surface.

13. The liquid-absorbent structure defined by claim 12, wherein said liquid-absorbent core material comprises at least absorbent polymer particles.

14. The liquid-absorbent structure defined by claim 11, wherein said liquid-absorbent core material comprises at least absorbent polymer particles.

15. The liquid-absorbent structure defined by claim 11, wherein
said second sheet is additionally formed on said second outer surface with a high density liquid-absorbent structure;
said first and second sheets are liquid-pervious;
said high density liquid-absorbent structure comprises liquid-absorbent core material and a wrapping sheet used to wrap said liquid-absorbent core material, said high density liquid-absorbent structure being at least partially formed with high density regions having a density higher than that in the remaining region of said liquid-absorbent core material.

16. The liquid-absorbent structure defined by claim 1, wherein
said first sheet lies on a side facing the wearer's body and said second sheet lies on a side opposed to said side facing said wearer's body; and
said first and second sheets respectively have first side edges and second side edges extending in said longitudinal direction in such a manner that said second side edges extend outward beyond said first side edges in said transverse direction and portions of said second sheet extending beyond said first side edges are folded back along said first side edges onto said first outer surface and bonded to said first outer surface.

17. The liquid-absorbent structure defined by claim 16, wherein said liquid-absorbent core material comprises at least absorbent polymer particles.

18. The liquid-absorbent structure defined by claim 1, wherein said liquid-absorbent core material comprises at least absorbent polymer particles.

19. The liquid-absorbent structure defined by claim 1, wherein
said second sheet is additionally formed on said second outer surface with a high density liquid-absorbent structure;
said first and second sheets are liquid-pervious;
said high density liquid-absorbent structure comprises liquid-absorbent core material and a wrapping sheet used to wrap said liquid-absorbent core material, said high density liquid-absorbent structure being at least partially formed with high density regions having a density higher than that in the remaining region of said liquid-absorbent core material.

20. The liquid-absorbent structure defined by claim 19, wherein said high density regions in said high density liquid-absorbent structure overlap at least one of said first and second non-bonding regions.

* * * * *